(12) United States Patent
Saul

(10) Patent No.: US 7,025,739 B2
(45) Date of Patent: Apr. 11, 2006

(54) SYSTEM AND METHOD FOR TREATING ELEVATED INTRACRANIAL PRESSURE

(75) Inventor: Tom Saul, El Granada, CA (US)

(73) Assignee: Integra LifeSciences Corporation, Plainsboro, NJ (US)

( * ) Notice: Subject to any disclaimer, the term of this patent is extended or adjusted under 35 U.S.C. 154(b) by 365 days.

(21) Appl. No.: 10/215,059

(22) Filed: Aug. 7, 2002

(65) Prior Publication Data
US 2003/0032915 A1    Feb. 13, 2003

Related U.S. Application Data

(60) Provisional application No. 60/311,307, filed on Aug. 9, 2001.

(51) Int. Cl.
*A61M 5/00* (2006.01)
(52) U.S. Cl. ............................... 604/9; 604/8
(58) Field of Classification Search ............. 604/8–10, 604/6.16, 264, 247, 533, 27, 28, 335, 30, 604/246, 256, 43, 523, 537, 93.01; 600/561; 137/455, 458, 511
See application file for complete search history.

(56) References Cited

U.S. PATENT DOCUMENTS

| | | | |
|---|---|---|---|
| 3,886,948 A * | 6/1975 | Hakim | 604/9 |
| 3,889,687 A | 6/1975 | Harris et al. | |
| 3,913,587 A | 10/1975 | Newash | |
| 3,985,140 A | 10/1976 | Harris | |
| 4,375,816 A | 3/1983 | Labianca | |
| 4,377,169 A | 3/1983 | Banks | |
| 4,385,636 A | 5/1983 | Cosman | |
| 4,432,853 A | 2/1984 | Banks | |
| 4,532,932 A | 8/1985 | Batty, Jr. | |
| 4,540,400 A | 9/1985 | Hooven | |
| 4,551,128 A | 11/1985 | Hakim et al. | |
| 4,557,721 A | 12/1985 | Hooven | |
| 4,576,035 A | 3/1986 | Hooven et al. | |
| 4,595,390 A | 6/1986 | Hakim et al. | |
| 4,598,579 A | 7/1986 | Cummings et al. | |
| 4,601,724 A | 7/1986 | Hooven et al. | |

(Continued)

FOREIGN PATENT DOCUMENTS

EP    0 421 558    4/1995

(Continued)

OTHER PUBLICATIONS

Chapman et al., "The Relationship Between Ventricular Fluid Pressure and Body Position in Normal Subjects and Subjects With Shunts: A Telemetric Study," *Neurosurgery,* (1990) vol. 26(2) pp. 181-189.

(Continued)

*Primary Examiner*—Patricia Bianco
*Assistant Examiner*—Leslie R. Deak
(74) *Attorney, Agent, or Firm*—Caesar, Rivise, Bernstein, Cohen & Pokotilow, Ltd.

(57) ABSTRACT

Methods and systems for lowering elevated intracranial pressure utilizing a fluid drainage controller which regulates the drainage of cerebral spinal fluid based on a cardiac or other transient component of the patient's intracranial pressure. The cardiac component of the intracranial pressure increases as the accumulation of cerebral spinal fluid in the patient's subarachnoid space increases, but is not directly a function of the absolute mean or baseline intracranial pressure. Thus, control based on the cardiac component is relatively independent of patient position and the risk of over or under draining the cerebral spinal fluid is lessened.

17 Claims, 8 Drawing Sheets

U.S. PATENT DOCUMENTS

| | | | |
|---|---|---|---|
| 4,627,832 A | 12/1986 | Hooven et al. | |
| 4,631,051 A | 12/1986 | Harris | |
| 4,675,003 A | 6/1987 | Hooven | |
| 4,676,772 A | 6/1987 | Hooven | |
| 4,681,559 A | 7/1987 | Hooven | |
| 4,705,499 A | 11/1987 | Hooven | |
| 4,714,458 A | 12/1987 | Hooven | |
| 4,714,459 A | 12/1987 | Hooven | |
| 4,769,002 A | 9/1988 | Hooven | |
| 4,776,838 A | 10/1988 | Sainte-Rose et al. | |
| 4,781,672 A | 11/1988 | Hooven | |
| 4,787,886 A | 11/1988 | Cosman | |
| 4,850,955 A | 7/1989 | Newkirk | |
| 4,861,331 A | 8/1989 | East et al. | |
| 4,867,740 A | 9/1989 | East | |
| 4,931,039 A | 6/1990 | Coe et al. | |
| 4,950,232 A | 8/1990 | Ruzicka et al. | |
| 5,039,511 A | 8/1991 | Quay et al. | |
| 5,069,663 A | 12/1991 | Sussman | |
| 5,336,166 A | 8/1994 | Sierra | |
| 5,368,556 A | 11/1994 | Lecuyer | |
| 5,385,541 A | 1/1995 | Kirsch et al. | |
| 5,387,188 A | 2/1995 | Watson | |
| 5,405,316 A * | 4/1995 | Magram | 604/8 |
| 5,437,827 A | 8/1995 | Marx | |
| 5,458,606 A | 10/1995 | Cohen et al. | |
| 5,643,195 A | 7/1997 | Drevet et al. | |
| 5,928,182 A * | 7/1999 | Kraus et al. | 604/9 |
| 5,980,480 A | 11/1999 | Rubenstein et al. | |
| 6,533,733 B1 * | 3/2003 | Ericson et al. | 600/561 |

FOREIGN PATENT DOCUMENTS

| | | |
|---|---|---|
| EP | 0 798 011 | 1/1997 |
| EP | 0 798 012 | 10/1997 |
| SE | 880 1516 | 4/1988 |
| SU | 129 7870 | 3/1987 |
| WO | WO 96/28200 | 9/1996 |

OTHER PUBLICATIONS

Condon et al., "A Quantitative Index of Ventricular and Extraventricular Intracranial CSF Volumes Using MR Imaging," *Journal of Computer Assisted Tomography,* (1986) vol. 10(5) pp. 784-792.

Condon et al., "MR Relaxation Times of Cerbrospinal Fluid," *Journal of Computer Assisted Tomography,* (1987) vol. 11(2), pp. 203-207.

Czosnyka et al., "Posture-related Overdrainage: Comparison of the Performance of 10 Hyrocephalus Shunts in Vitro," *Neurosurgery,* (1998) vol. 42 (2) pp. 327-334.

Langfitt, Thomas W., M.D., "Clinical Methods For Monitoring Intracranial Pressure and Measuring Cerebral Blood Flow," *Clinical Neurosurgery: Proceedings of the Congress of Neurological Surgeons,* (1974) Chapter 17, pp. 302-320.

Magnaes Bjørn, M.D., "Body Position and Cerebrospinal Fluid Pressure," *J. Neurosurgery* (1976) vol. 44, pp. 698-705.

* cited by examiner

SYSTEM AND METHOD FOR TREATING ELEVATED INTRACRANIAL PRESSURE

CROSS-REFERENCES TO RELATED APPLICATIONS

This application claims the benefit of provisional application No. 60/311,307, filed on Aug. 9, 2001, the full disclosure of which is incorporated herein by reference.

BACKGROUND OF THE INVENTION

1. Field of the Invention

The present invention relates generally to medical devices and methods. More particularly, the present invention relates to improved systems and methods for removing or draining cerebral spinal fluid (CSF) from a subarachnoid or CSF space of a patient to control intracranial pressure (ICP) and/or modulate CSF hydrodynamics to treat hydrocephalous and other diseases.

Hydrocephalus is a condition characterized by an elevated ICP resulting from excessive production or retention of CSF in the patient's CSF space (as defined hereinafter). Hydrocephalus is commonly treated by implanting a shunt to provide controlled drainage of the CSF from the CSF space. In particular, the shunt comprises a tube having one end implanted in the patient's cerebral ventricles and another end implanted in a location outside of the CSF space to which the CSF can be drained, such as the peritoneum. The shunt typically comprises a control valve positioned along its length to control flow based on the differential pressure between the ventricles and the peritoneum. As excess CSF accumulates in the CSF space, the pressure in the ventricles and elsewhere increases. The control valve of the shunt is typically arranged to open when the differential pressure exceeds some threshold value. Thus, the shunt acts as a pressure relief system for the CSF space including the subarachnoid spacing (as defined hereinbelow).

Although quite successful for treating hydrocephalus, such shunts can have problems under certain circumstances. In particular, because the amount of CSF drained from the ventricles depends on the differential pressure across the control valve, patient position can have a significant effect on the amount of fluid being drained. In some instances, too much CSF can be drained causing the patient's ICP to fall below desirable levels. The problem arises because conventional hydrocephalus shunts have valves which control the differential pressure across the valve. While excessive production or inadequate drainage of CSF is one cause of the pressure building up in the ventricles, changes in patient position will also affect the differential pressure. The control valve has no way of distinguishing between these two sources of pressure variation, so the valves must be set to operate at a control pressure point which is a comprise between maintaining a target pressure in the ventricles and providing a margin of safety so that the valve will not drain excess CSF in response to patient movement. Moreover, other safety devices often must be added to the hydrocephalus shunts to further protect the patients, such as anti-gravity devices, and the like. With all these precautions, it is very difficult to maintain the target pressure in the ventricles and over drainage and under drainage of the CSF frequently occurs.

For these reasons, it would be desirable to provide improved systems and methods for controlling ICP in order to treat hydrocephalus and other conditions associated with elevated ICP or excessive production of CSF and other conditions associated with compromised CSF drainage and hydrodynamics. In particular, such systems and methods should remove CSF in a manner which is not dependent on patient position or posture and more closely maintain a natural ICP. Such systems and methods would thus provide for maintenance of ICP within more desirable physiologic levels, and should reduce the risk of over and under drainage of CSF and excessive lowering of ICP. Still more desirably, such systems and methods could be implemented in a variety of ways, including mechanically, hydraulically, electronically, and combinations thereof. At least some of these objectives will be met by the inventions described hereinbelow.

2. Description of the Background Art

Conventional devices for draining CSF in response to baseline ICP are described in numerous prior patents, including U.S. Pat. Nos. 3,889,687; 3,985,140; 3,913,587; 4,375,816; 4,377,169; 4,385,636; 4,432,853; 4,532,932; 4,540,400; 4,551,128; 4,557,721; 4,576,035; 4,595,390; 4,598,579; 4,601,721; 4,627,832; 4,631,051; 4,675,003; 4,676,772; 4,681,559; 4,705,499; 4,714,458; 4,714,459; 4,769,002; 4,776,838; 4,781,672; 4,787,886; 4,850,955; 4,861,331; 4,867,740; 4,931,039; 4,950,232; 5,039,511; 5,069,663; 5,336,166; 5,368,556; 5,385,541; 5,387,188; 5,437,627; 5,458,606; PCT Publication WO 96/28200; European Publication 421558; 798011; and 798012; French Publication 2 705 574; Swedish Publication 8801516; and SU 1297870. A comparison of the pressure-flow performance of a number of commercially available hydrocephalus shunt devices is presented in Czosnyka et al. (1998) *Neurosurgery* 42: 327–334. A shunt valve having a three-stage pressure response profile is sold under the Orbis-Sigma® tradename by Nitinol Medical Technologies, Inc. Boston, Mass. 02210 (formerly by Cordis). U.S. Pat. No. 5,334,315, describes treatment of various body fluids, including cerebrospinal fluids, to remove pathogenic substances therefrom. Articles discussing pressures and other characteristics of CSF in the CSF space include Condon (1986) *J. Comput. Assit. Tomogr.* 10:784–792; Condon (1987) *J. Comput. Assit. Tomogr.* 11:203–207; Chapman (1990) *Neurosurgery* 26:181–189; Magneas (1976) *J. Neurosurgery* 44:698–705; Langfitt (1975) *Neurosurgery* 22:302–320.

BRIEF SUMMARY OF THE INVENTION

In a first specific aspect to the present invention, intracranial pressure in a patient is maintained at an acceptable or "normal" level (which will usually be lower than the unregulated pressure), usually for the treatment of hydrocephalous or other conditions related to chronic or intermittent pathological elevation of intracranial pressures. The method relies on sensing a transient component of the intracranial pressure, typically a "cardiac" or "respiratory" component, as discussed in detail below. The magnitude of the transient component changes as the baseline ICP changes, but will generally be free from significant variations caused by changes in patient position or posture. Thus, the magnitude of the transient component of ICP can be used as a control point for maintaining the baseline ICP within acceptable limits while minimizing the influence of changes in the baseline ICP resulting from changes in the position of the patient, e.g. reclining, standing, or otherwise.

The transient component of the patient's intracranial pressure is sensed, preferably continuously or at least frequently, so that cerebral spinal fluid drainage from the CSF space can be established or increased in response to observed increases in the magnitude of the sensed transient component of the patient's ICP. In this way, spinal fluid can be drained in a manner that is not directly related to the baseline pressure component measured at any particular point in the CSF space.

Apparatus according to the present invention could take a variety of forms. Generally, the apparatus will comprise an implantable control structure having an input for receiving cerebral spinal fluid from a patient's subarachnoid space and an output for draining the cerebral spinal fluid to a location outside of the subarachnoid space, typically to the peritoneal cavity. The implantable control structure will include a valve or other fluid control mechanism connected to control cerebral spinal fluid flow between the input and output of the controller structure. The valve will allow drainage in response to an increase in the magnitude of transient component of the patient's intracranial pressure. The valve will also close or reduce flow in response to a decrease in the magnitude of the transient component. Typically, the valve will remain closed until the magnitude of the transient component of the intracranial pressure exceeds a predetermined minimum level, e.g., in the case of the cardiac component, usually in the range from 1 mmHg to 10 mmHg, typically about 2 mmHg. The valve can then open completely over a predetermined pressure range.

Control of the valve can be achieved in a variety of ways. In some instances, it will be possible to utilize an electronic or fluidic feedback control system, where the valve can be electrically, hydraulically, or mechanically operated. In an exemplary embodiment of the present invention, the implantable controller structure will include a first chamber which is exposed to patient CSF to sense the "real time" ICP, i.e. the varying pressure within the CSF space including the cardiac component and the breathing component superimposed over the baseline. The structure will also include a second chamber which is maintained at the average of the real time intracranial pressure and/or in which the transient component is out of phase with pressure changes in the first chamber, e.g. a chamber which is attached to the first chamber through a fluid resistor which in conjunction with internal system capacitance dampens the variation to approximate the desired average level. The second chamber "filter" the input pressure wave, typically by incorporating capacitance and resistance elements. This filter behaves as a signal averaging mechanism wherein the cardiac pressure component is averaged while the mean pressure is transmitted to the chamber. The residual cardiac component observed in the second chamber will usually also be phase shifted from the input signal. These actions will be referred to as "averaging" from here on. The valve can then be coupled to the chambers to sense the differential pressure therebetween. The differential pressure will generally correspond to the cardiac component of the intracranial pressure, e.g. the pressure in the first chamber minus the pressure in the second chamber. The valve will then open whenever this differential pressure exceeds the predetermined threshold level. Thus, the valve will be opening at a frequency which generally corresponds to the frequency of the cardiac or breathing components of intracranial pressure.

DETAILED DESCRIPTION OF THE INVENTION

Figure 1:
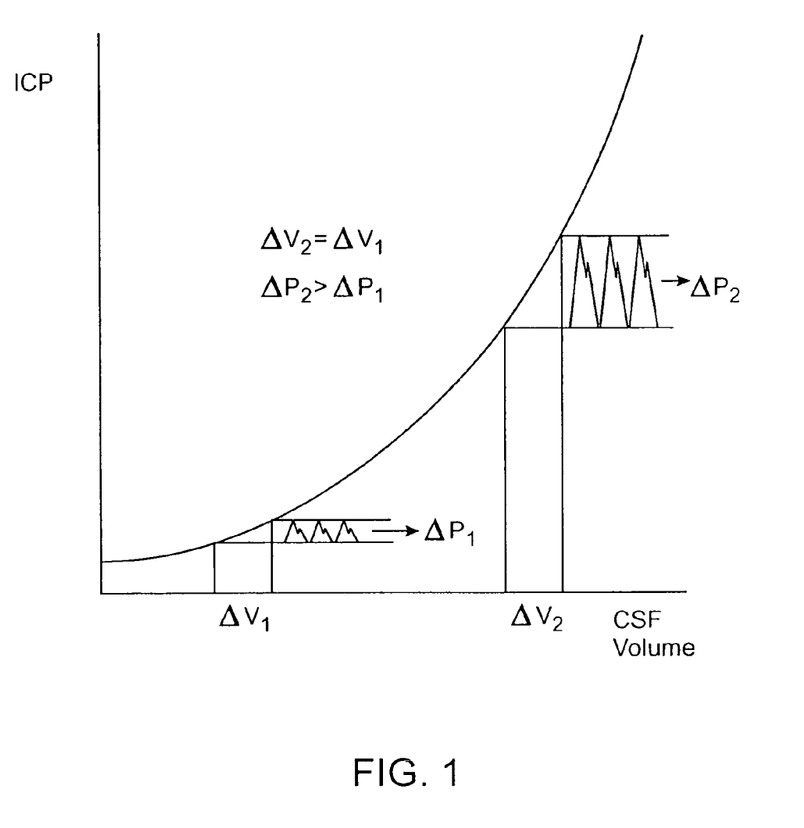
FIG. 1 illustrates the effect of induced changes in CSF volume on the cardiac component of ICP ($\Delta P$). The change in CSF volume ($\Delta V$) at two levels of ICP. The $\Delta P$ increases as CSF volume increases.

Intracranial pressure (ICP) can be considered to be the superposition of a mean "dc" pressure component (referred to hereinafter as the "baseline pressure") and an "ac" time varying pressure component (referred to hereinafter as the "transient component"). The transient component typically results from changes in the blood volume within the CSF space driven by the heart in association with the cardiac cycle and diaphragm in association with breathing. As such, the transient ICP component falls within well-understood limits associated with breathing and heart rates. While the cardiac and respiratory components of ICP are the best known and understood, there may be additional transient components from other origins. Usually, however, these transient components will not significantly affect the control protocols described hereinafter. Since the CSF space is essentially a closed system with a nonlinear pressure-volume relationship, the magnitude of the transient pressure component varies with the baseline, i.e., the transient component ICP waveform increases in magnitude as the ICP increases. An idealized representation of this relationship is depicted in FIG. 1 and actual data measured in man is presented in FIG. 2.

Figure 1A:
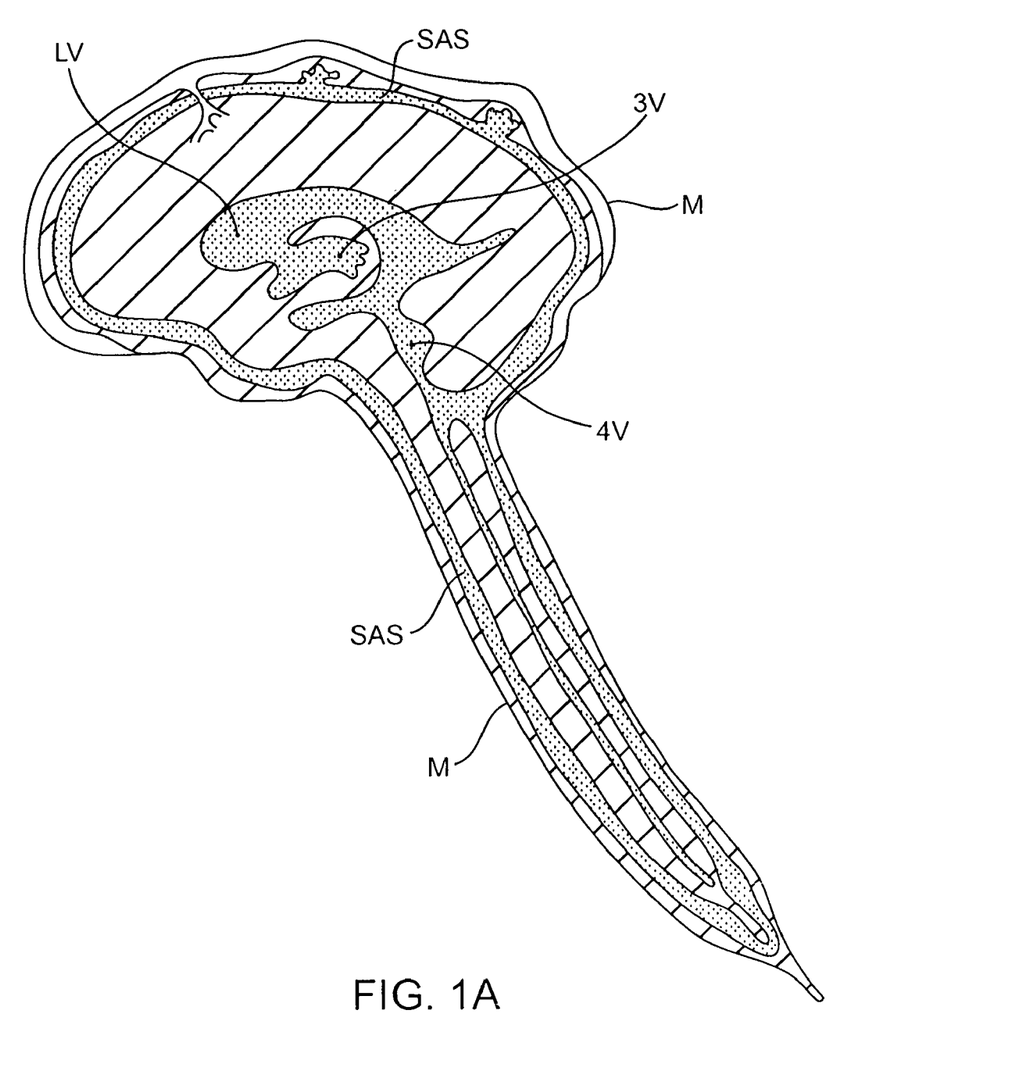
FIG. 1A illustrates the CSF space including the brain and the spinal column.

The CSF space is illustrated in FIG. 1A and includes all the volume within the meninges M which is the three-membrane complex enveloping the brain and spinal cord. The brain and spinal cord are bathed in cerebrospinal fluid (CSF) and encased within the cranium and vertebral column inside the meninges. The CSF space within the meninges includes the subarachnoid space SAS, the ventricles (including the lateral ventricle LV, third ventricle 3V, and fourth ventricle 4V), the vertebral column, and the brain interstitial spaces. Sometimes the phrase "subarachnoid space" is used to describe the entire volume within the meninges, and to that extent the phrases "CSF space" and subarachnoid space may be synonymous. The volume of the brain intracranial spaces is on average about 1700 ml. The volume of the brain is approximately 1400 ml, and the volume of the intracranial blood is approximately 150 ml. The remaining 150 ml is filled with CSF (this volume will typically vary within 60 ml to 290 ml). The CSF circulates within the CSF space. CSF is formed principally by the choroid plexuses, which secrete about 80% of the total volume of the CSF. The sources of the remainder are the vasculature of the subependymal regions, and the pia matter. The total volume of the CSF is renewed several times per day, so that about 500 ml are produced every 24 hours (equivalent to about 20 ml/hr or 0.35 ml/min) in healthy adults. The production rate varies in the old, the young in certain diseases.

The cerebrospinal fluid is absorbed through the arachnoid villi, located principally over the superior surfaces of the cerebral hemispheres. Some villi also exist at the base of the brain and along the roots of the spinal nerves. The absorptive processes include bulk transport of large and small molecules and as well as diffusion across porous membranes of small molecules. The production and absorption of CSF are well described in the medical literature. See, e.g., Adams et al. (1989) "Principles of Neurology," pp. 501–502.

The meninges thus acts as a compliant membrane or envelope which contains the CSF. As the CSF is liquid and incompressible, increases in CSF volume within the meninges, i.e., within the CSF space, will thus result in a stretching or enlargement of the meninges. As the CSF volume continues to increase, however, the compliance decreases so that equal incremental volume increases ($\Delta V$) result in larger incremental increases in ICP ($\Delta P$), as illustrated in FIG. 1. In particular, FIG. 1 plots patient ICP vs. CSF volume in the absence of patient positional changes. The partially compliant nature of the meninges and vasculature results in the non-linear (curved) relationship which is shown. For the purposes of the present invention, it is most significant that an incremental change in CSF volume at relatively low total CSF volumes ($\Delta V_1$) will produce an incremental change in the observed ICP ($\Delta P_1$), which is much less than the observed change in ICP ($\Delta P_2$), which results from an identical incremental change in CSF volume ($\Delta V_2$), which occurs at higher ICPs which result from higher total CSF in the CSF space. Thus, by measuring or otherwise detecting such larger $\Delta P$'s, the pressure of CSF in the CSF space can be modulated and controlled in a manner which is relatively independent of the observed mean ICP. This is advantageous since changes in ICP may result from changes in patient position even when there has been no change in the actual CSF volume or CNS compliance within the CSF space. Thus, when treating hydrocephalus or other conditions associated with the excessive production or retention of CSF, the CSF can be drained when the CSF volume has increased but generally not when ICP has been elevated for other reasons.

Figure 2:
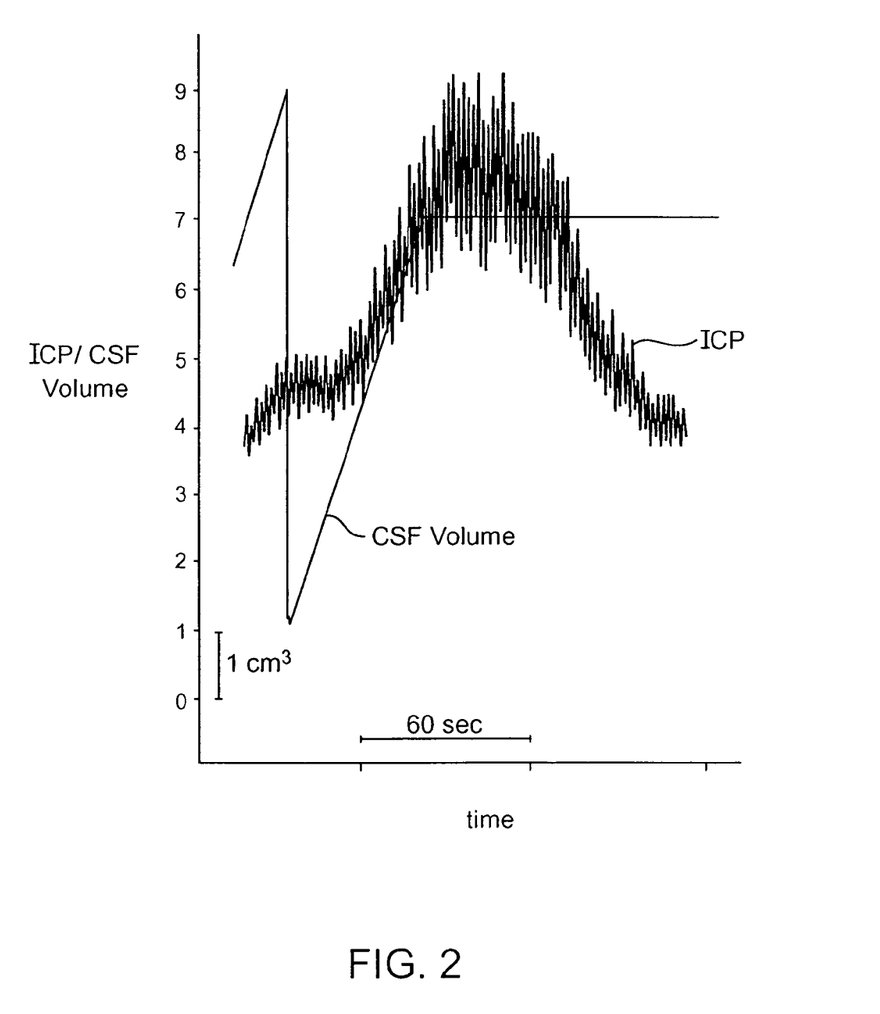
FIG. 2 is a graph of intracranial pressure and volume input over time showing the transient ICP component (cardiac component). The solid line indicates the CSF volume ($cm^3$).

FIG. 1 is a theoretical representation of the relationship between ICP and changes in the CSF volume which result in changes in the CNS compliance. FIG. 2 is an actual plot of ICP and introduced CSF volume measured in a patient having mock CSF introduced to the patient's CSF space over time. FIG. 2 clearly illustrates the rise in both ICP and the increase in the $\Delta P$ resulting from the cardiac component of ICP as the CSF volume increases and the CNS compliance decreases.

Figure 2A:
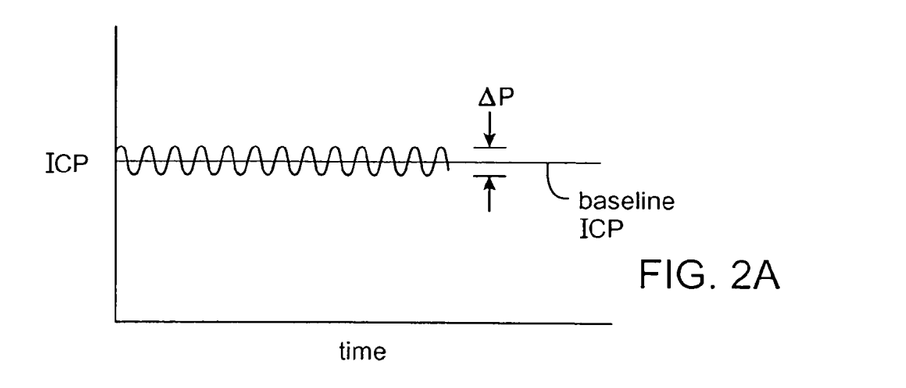
FIG. 2A is an idealized graph showing the transient component of ICP of a patient whose position has not changed and whose CSF volume has not changed.
Figure 2B:
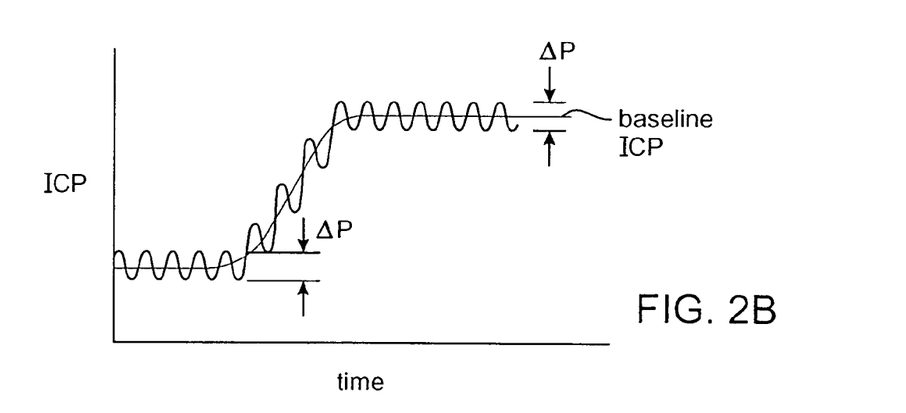
FIG. 2B is an idealized graph showing the transient component of CNS/ICP of a patient who has reclined but whose CNS/CSF volume has remained constant.
Figure 2C:
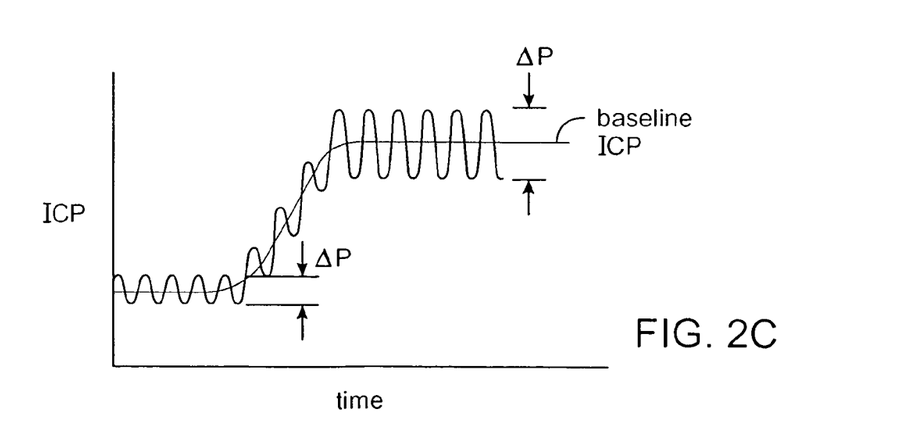
FIG. 2C is an idealized graph showing the transient component of ICP of a patient whose CNS/CSF volume has increased but whose position has remained constant.

Referring now to FIGS. 2A–2C, the variation in baseline in transient ICP under three different circumstances will be described. In FIG. 2A, ICP in a patient whose CSF volume is not increasing and who is not changing position is illustrated. In such cases, both the baseline ICP and the transient component of ICP ($\Delta P$) will remain constant. The transient component of ICP which is illustrated is generic to the cardiac component and respiratory component which would actually be observed in a patient. The magnitudes and frequencies of these two components would vary and would be distinct from each other, thus leading to a complex actual waveform superimposed upon the baseline ICP pressure trace. Of the two components, it will usually be preferable to rely on the cardiac component which will generally be changed less in magnitude and frequency. In the control systems described hereinafter, it is possible at least to a certain extent to provide for electronic fluidic filtering in order to isolate the cardiac component which will have a normal cardiac frequency, from 60 to 90 beats per minute.

In FIG. 2B, the ICP of a patient who has reclined is illustrated. In that instance, the baseline ICP increases (at least assuming that the ICP is being measured in the ventricles), but the transient component of ICP ($\Delta P$) remains relatively constant.

In FIG. 2C, the ICP of a patient whose CSF volume has increased due to hydrocephalus or other causes but whose position has not changed is illustrated. In that instance, both the baseline ICP and the transient component of ICP ($\Delta P$) increase. Thus, it can be seen that by observing changes in the transient component of ICP ($\Delta P$), patients having a rise in baseline ICP resulting from an increase in CSF volume can be distinguished from those having a rise in ICP resulting from positional changes. As described in more detail below, the methods and apparatus of the present invention can thus selectively drain or remove CSF from only those patients whose ICP rise results from an increase in CSF volume.

Figure 3:
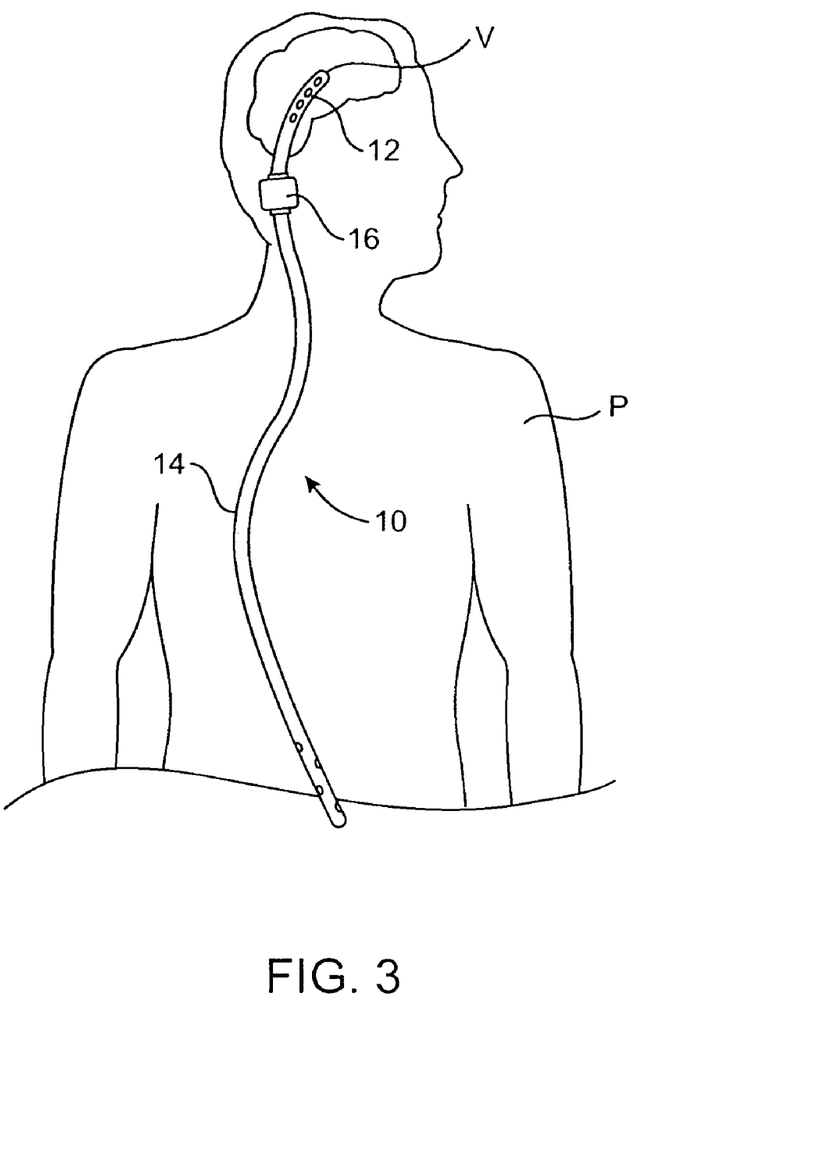
FIG. 3 illustrates the implantation of cerebral spinal fluid drainage shunt and controller in a patient to drain CSF from the CSF space of the patient.

Referring now to FIG. 3, a patient suffering from hydrocephalous or another condition relating to elevated intracranial pressures, will have a catheter system 10 implanted in order to drain cerebral spinal fluid from the CSF space, typically from a location in the patient's ventricles V. Typically, a ventricular or drain catheter 12 is implanted in the ventricles and a peritoneal or discharge catheter 14 is implanted to drain into a location, such the peritoneal cavity. A flow controller 16 having an input and an output is connected between the drain catheter and disposal catheter. To this point, description of the system 10 is generally conventional, and the present invention is found in the particular pressure-response characteristics of the flow controller 16 structure.

Figure 3A:
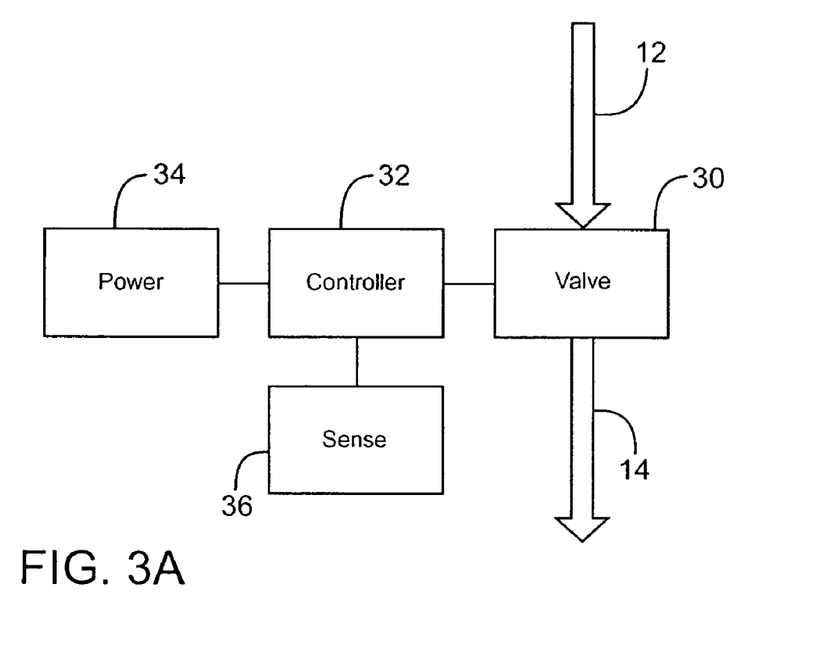
FIG. 3A is a schematic diagram illustrating a control system according to the principles of the present invention.

Referring to FIG. 3A, systems according to the present invention for the controlled drainage of CSF from a patient's CSF space based on changes in the transient component of patient ICP may comprise a control valve or other flow control element 30 disposed between a ventricular catheter 12 and peritoneal catheter 14, as generally shown in FIG. 3. Optionally, a source of power 34 may be provided, and some mechanism, transducer, electrical circuitry, fluidic circuitry, or the like, will be provided for sensing ICP to permit a mechanical, hydraulic, fluidic, or electrical controller to operate the valve 30. In particular, the controller 32 will be constructed or programmed to open the valve 30 in response to increases in the transient component of patient ICP and to close the valve in response to decreases in the transient component. The details of the implementation may vary widely, but generally the valve 30 will be opened when the transient component of ICP, usually the cardiac component, exceeds a value in the range from 1 mmHg to 10 mmHg, usually from 2 mmHg to 5 mmHg. The exemplary value for opening an on-off valve is when the cardiac component exceeds 3 mmHg. The flow rate provided by opening the valve 30 is less critical since the valve may be maintained open for periods sufficiently long to drain a volume of CSF needed to lower the transient component of ICP beneath the control value. Usually, however, the valve will be configured to permit a drainage flow rate in the range from 1.5 ml per hour to 42 ml per hour, usually from 3 ml per hour to 21 ml per hour, when patient ICP is in the range from −17 mmHg to 40 mmHg.

Figure 3B:
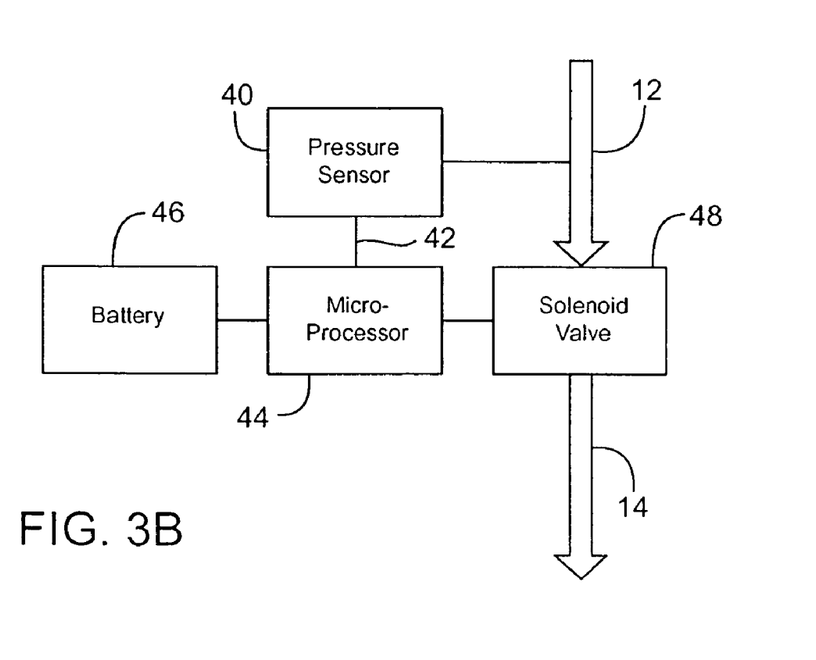
FIG. 3B is a schematic diagram illustrating an exemplary control system which employs an electronic controller according to the principles of the present invention.

Referring now to FIG. 3B, an electronic system for draining CSF in accordance with the principles of the present invention is illustrated. The system is generally a self-contained battery-powered unit, where the battery is optionally rechargeable, e.g., using transcutaneously directed radiofrequency energy. A pressure sensor 40 may be a conventional pressure transducer, such as a capacitate coupled diaphragm, and may be located on the ventricular catheter 12, either at its distal end which is implanted within the ventricle or elsewhere where it may be fluidly coupled to a pressure-detection lumen within the catheter. An electrical output 42 of the pressure sensor is fed to controller 44, which is typically a solid state digital controller, e.g., a microprocessor or gate array, but which could also be an analog controller. The controller 44 and pressure sensor 40 are powered through the battery 46, and the output of the controller 44 drives flow control element 48, typically a solenoid valve, disposed between the ventricular catheter 12 and peritoneal catheter 14. Typically, to save energy, the solenoid valve will be powered to open and will close in the absence of power. Alternatively, for safety, it may be preferable to power the solenoid valve closed, but that approach will decrease battery life.

The microprocessor or analog controller 44 may be programmed to operate the solenoid value based on a variety of algorithms. For example, the controller may be programmed to open the solenoid valve when the peak-to-peak change in ICP ($\Delta P$) exceeds a pre-determined valve, such as those set forth above. The controller may then maintain the valve open for a pre-determined period of time, such as 10 to 80 seconds, usually 20 to 40 seconds, or may close the valve only after $\Delta P$ have returned to an acceptable level. Alternatively, the controller 44 may be programmed to monitor the rate of change in ICP, and control drainage in response.

In all implementations, it will usually be desirable that the valve 30 or solenoid valve 48 be flow limited or be placed in series with a flow limiting element. In that way, the risk of catastrophic excess CSF drainage can be reduced. Additionally, it may be desirable to provide for fail-safe operation where the valve 30 or 48 closes in the case of loss of power or other malfunction. In such instances, it would be particularly desirable if the system could provide an alarm or signal of the malfunction. Optionally, the devices could have other safety features, such as a flow monitor which could provide an early indication of when the device was beginning to fail. Such a monitor could most easily be implemented in the electronic control systems described herein where fluid flow could be measured and/or the accumulation of flow over time could be determined and variations from acceptable ranges could then be transmitted to an external sensor, for example at the time the device is externally recharged.

Figure 4:
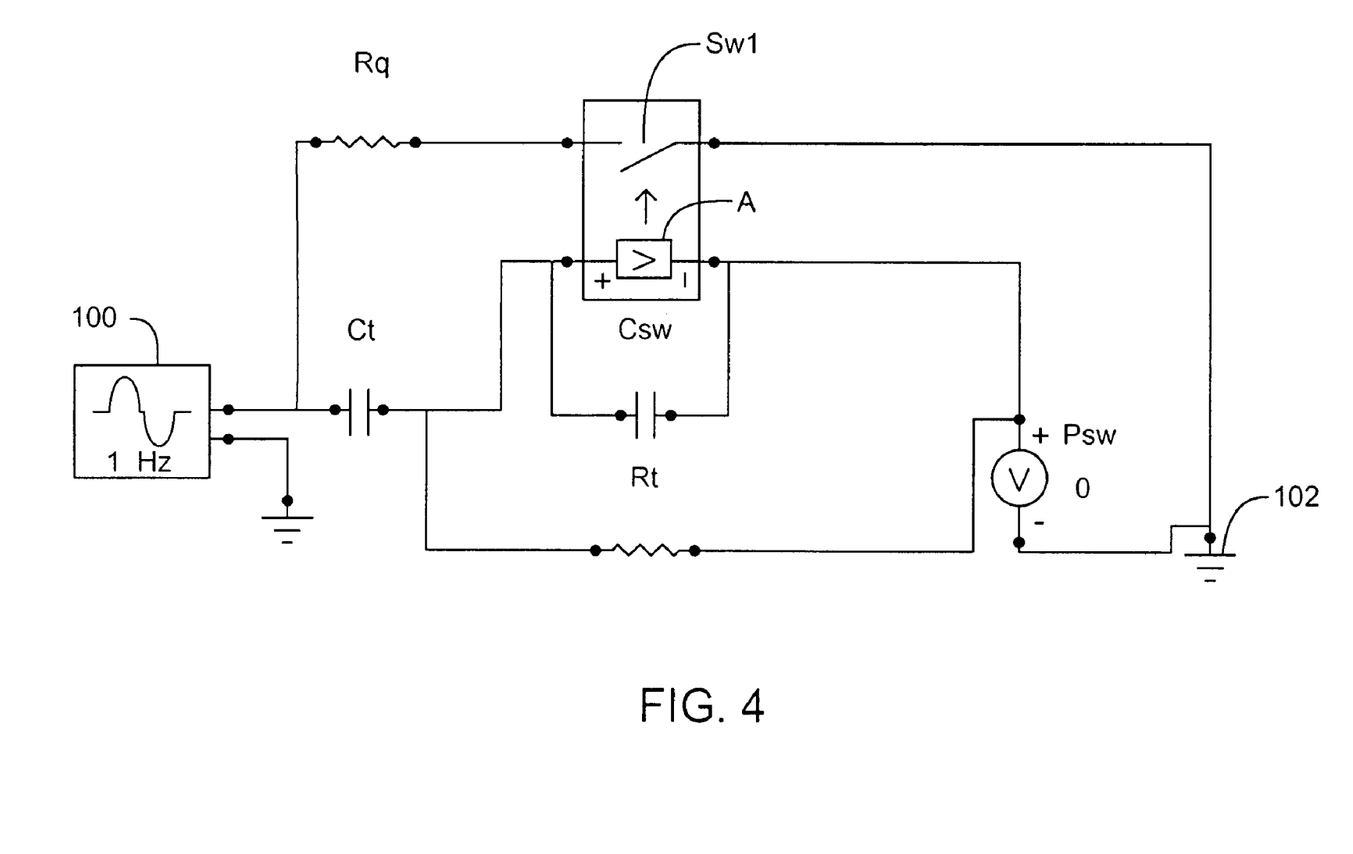
FIG. 4 illustrates en electrical circuit analog of an exemplary control system of the present invention.
Figure 5:
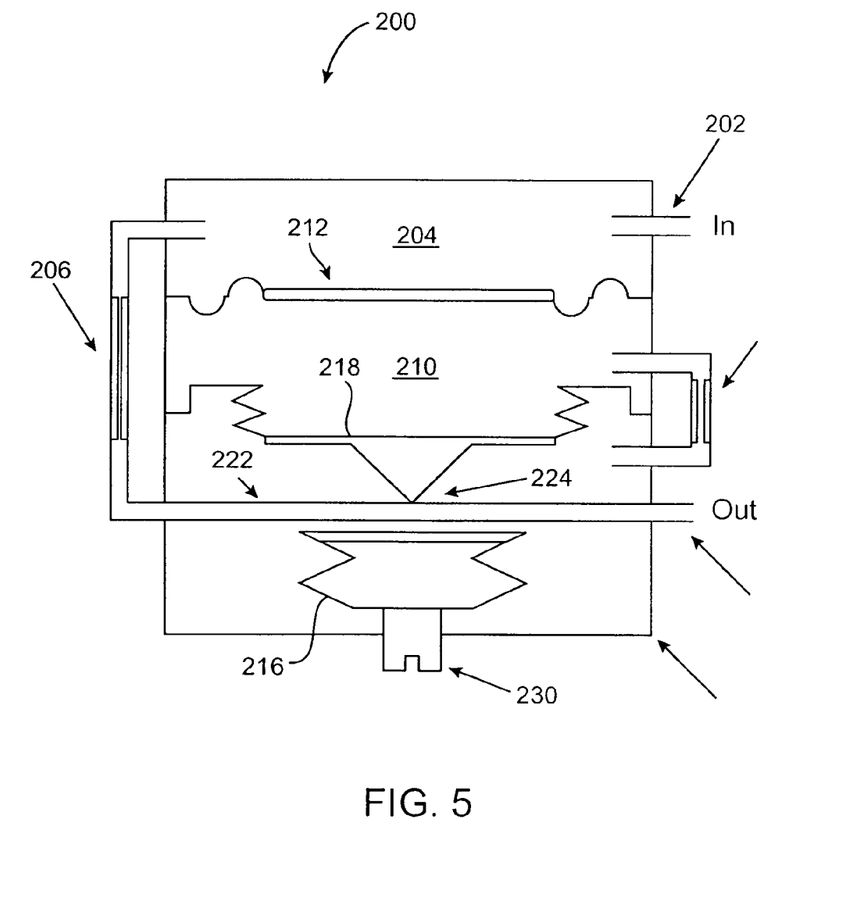
FIG. 5 illustrates a construction of an exemplary flow controller constructed in accordance with the principles of the present invention.

A fluidic flow controller suitable for use in the present invention is described in FIGS. 4 and 5. FIG. 4 is an electrical analogy to the fluidic system illustrated in FIG. 5. In FIG. 4, a CSF source, typically one of the lateral ventricles (indicated by the signal generator 100), feeds to a fluid resistor Rq and fluid capacitor Ct and resistor Rt. Fluid flows through Rq to a sink, indicated by the ground 102, typically the peritoneal cavity, when switch Sw1 (valve) is in the on condition. The fluid resistance of Rq is chosen such that the maximum flow through the device will be less than some maximum for reasons of safety. SW1 is coupled to an actuator A which closes the switch (opens the valve) when a differential pressure greater than a threshold value is experienced across the switch control. Capacitor Csw is included to account for the capacitance associated with a physical implementation of the switch control. The actuator A is coupled to the input by fluid capacitor Ct. In this fashion, only time-varying pressures will be experienced across the actuator of SW1. Ct and Rt are chosen such that when time-varying source signals are greater in frequency than, for example, 08 Hz and greater in magnitude than, for example 1 mmHg, the peak pressure generated across Rt and the actuator A is greater than or equal to the target threshold $\Delta P$. In this fashion SW1 is allowed to open for some portion of the period of time over which this condition persists. As such, for time-varying signals that do not meet these conditions, SW1 is not activated and no or minimal flow occurs across the device. As the magnitude of the time-varying signal increases, the "on time" for SW1 increases thereby allowing for a higher rate of flow.

A description of a particular mechanical implementation 200 of the system of FIG. 4 and the correspondence between the electrical analog follows.

Fluid is fed through input port 202 into chamber 204 and to a resistive fluid flow path 206 equivalent to Rq. Chambers 204 and 210 are separated by bellows diaphragm 212 and are equivalent to capacitor Ct. Fluid capacitance Ct of chambers 204 and 210 is predominantly characterized by the pressure/volume relationship associated with bellows 216 and the force displacement relation associated with a bellows diaphragm 218. Resistive flow path 220 corresponds to $R_t$. The valve actuator comprises flexible tubing 222, the upper surface of bellows 218 and a wedge 224 on the bottom of bellows 218. For pressures with time-varying components less than those associated with the cardiac cycle or other transient ICP component, the pressure differential generated across bellows 218 by deformation of bellows 212 will be minimal and the valve actuator will remain closed. For pressures changes with frequencies in the target ranges characteristic of cardiac and other transient ICP components, intermittent pressures across bellows 218 will be sufficient to unpinch tube 222. The pressure differential necessary to maintain this condition however will be dissipated through flow path 220 and the valve will close. Mechanism 230 allows for the adjustment of the closing force beneath the tube 222, which in turn allows adjustment of the opening pressure for the valve actuator.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for controlling intracranial pressure (ICP) in a patient, said method comprising:
   providing an implantable system including a mechanical sensor, a mechanical valve, and a mechanical linkage which opens the valve;
   wherein said sensor senses a transient component of the patient's ICP, said transient component being dependent on pressure changes due to changes in volume of cerebrospinal fluid (CSF) in the patient's CSF space and being independent of pressure changes related to patient position; and
   controlling the mechanical valve to control CSF drainage from the CSF space to maintain ICP in response to the sensed transient component of the ICP and generally independent of pressure changes related to patient position.

2. A method as in claim 1, wherein the transient component is a cardiac component.

3. A method as in claim 1, wherein the transient component is a respiratory component.

4. A method as in any of claim 1, 2, or 3, wherein sensing comprises sensing pressure in the ventricles.

5. A method as in any of claim 1, 2, or 3, wherein sensing comprises sensing pressure at a location in the CSF other than the ventricles.

6. A method as in any of claim 1, 2, or 3, wherein sensing comprises mechanically sensing the transient component of the patient's ICP.

7. A method as in any of claim 1, 2, or 3, wherein sensing comprises electronically sensing the transient component of the patient's ICP.

8. A method as in claim 7, wherein controlling drainage of CSF comprises providing an implantable system including (a) an electronic sensor, (b) electronic control circuitry for receiving a pressure signal from the electronic sensor, extracting a value of the transient component of the ICP, and producing a control signal, and (c) an electrically operated valve for controlling CSF drainage.

9. An improved method for draining cerebro spinal fluid (CSF) to treat hydrocephalus in a patient, said method comprising implanting a drainage conduit in the patient's CSF space to establish a drainage path from a location in a CSF space of the patient, wherein the improvement comprises modulating the volume of CSF drained through the drainage path in response to changes in a transient component of the patient's intracranial pressure (ICP), said transient component being dependent on pressure changes due to changes in volume of cerebrospinal fluid (CSF) in the patient's CSF space and being independent of pressure changes related to patient position.

10. An implantable flow control apparatus for controlling drainage of cerebrospinal fluid (CSF) from a CSF space in a patient, said apparatus comprising:
a pressure sensor configured to sense intracranial pressure (ICP) at a location in the patient's CSF space;
a flow control element adapted to modulate drainage of CSF from the CSF space; and
a control mechanism configured to adjust flow control element in response to a transient component of ICP sensed by the pressure sensor, said transient component being dependent on pressure changes due to changes in volume of cerebrospinal fluid (CSF) in the patient's CSF space and being independent of pressure changes related to patient position.

11. An apparatus as in claim 10, wherein the pressure sensor comprises a transducer with an electrical signal output and the control mechanism comprises an electrical circuit which produces a control output.

12. An apparatus as in claim 11, wherein the control output is an electrical signal and the control mechanism is an electrically operated valve.

13. An apparatus as in claim 11, wherein the control output is mechanical or fluidic and the control mechanism comprises a valve adapted to operate in response to a mechanical or fluidic output.

14. An apparatus as in claim 13, wherein the pressure sensor comprises a diaphragm having one side exposed to the ICP, the flow control element comprises a diaphragm, and the control mechanism comprises a fluidic circuit which exposes the other side of the diaphragm to baseline ICP substantially free from the transient component, wherein the one side of the diaphragm experiences a net pressure equal to the transient component of the ICP and wherein the diaphragm is balanced by spring force(s) which cause the diaphragm to open the flow control element when the magnitude of the transient component exceeds a set point value.

15. An apparatus as in claim 14, wherein the set point value is adjustable.

16. A cerebrospinal fluid (CSF) drainage controller comprising:
an implantable controller structure having an input for receiving CSF from a patient's subarachnoid space and an output for draining the fluid to a location outside the subarachnoid space; and
a valve connected within the structure to control the CSF flow between the input and the output, wherein the valve is configured to open in response to an increase in the magnitude of a cardiac component of the patient's intracranial pressure (ICP).

17. A CSF drainage controller as in claim 16, wherein the structure has first a chamber which is exposed to a real time ICP and a second chamber which is maintained at an average of the real time ICP, wherein the valve is coupled to the chamber to open and permit CSF flow when the average pressure exceeds the real time pressure by a threshold amount.

* * * * *